(12) United States Patent
Noh et al.

(10) Patent No.: US 7,763,882 B2
(45) Date of Patent: *Jul. 27, 2010

(54) ORGANIC LIGHT-EMITTING DEVICE COMPRISING BUFFER LAYER AND METHOD FOR FABRICATING THE SAME

(75) Inventors: Jeoung Kwen Noh, Daejeon Metropolitan (KR); Se Hwan Son, Daejeon Metropolitan (KR); Young Chul Lee, Daejeon Metropolitan (KR); Yun Hye Hahm, Daejeon Metropolitan (KR); Min Soo Kang, Daejeon Metropolitan (KR)

(73) Assignee: LG Chem, Ltd., Seoul (KR)

( * ) Notice: Subject to any disclaimer, the term of this patent is extended or adjusted under 35 U.S.C. 154(b) by 218 days.

This patent is subject to a terminal disclaimer.

(21) Appl. No.: 11/206,754

(22) Filed: Aug. 19, 2005

(65) Prior Publication Data

US 2006/0038484 A1 Feb. 23, 2006
US 2009/0058260 A9 Mar. 5, 2009

Related U.S. Application Data

(60) Continuation-in-part of application No. 10/798,584, filed on Mar. 10, 2004, now Pat. No. 7,538,341, which is a division of application No. 09/914,731, filed as application No. PCT/KR00/01537 on Dec. 27, 2000, now Pat. No. 6,720,573.

(30) Foreign Application Priority Data

Dec. 31, 1999 (KR) .............................. 1999-037746
Dec. 26, 2000 (KR) .............................. 2000-82085
Aug. 19, 2004 (KR) ....................... 10-2004-0065517

(51) Int. Cl.
*H01L 35/24* (2006.01)

(52) U.S. Cl. .................... 257/40; 257/E51.043; 438/82
(58) Field of Classification Search .................. 438/82; 257/40, E51.043
See application file for complete search history.

(56) References Cited

U.S. PATENT DOCUMENTS

| | | | |
|---|---|---|---|
| 4,356,429 A | 10/1982 | Tang | |
| 4,359,507 A | 11/1982 | Gaul et al. | |
| 4,769,292 A | 9/1988 | Tang et al. | |
| 4,780,536 A | 10/1988 | Czarnik et al. | |
| 5,150,006 A | 9/1992 | Van Slyke et al. | |
| 5,294,810 A | 3/1994 | Egusa et al. | |
| 5,366,811 A | 11/1994 | Higashi et al. | |
| 5,457,565 A | 10/1995 | Namiki et al. | |
| 5,540,999 A | 7/1996 | Yamamoto et al. | |
| 5,616,427 A | 4/1997 | Tada | |
| 5,645,948 A | 7/1997 | Shi et al. | |
| 5,766,779 A | 6/1998 | Shi et al. | |
| 5,792,568 A * | 8/1998 | Emoto et al. ............... | 428/690 |
| 5,811,833 A * | 9/1998 | Thompson ................... | 257/40 |
| 5,840,217 A | 11/1998 | Lupo | |
| 5,932,362 A * | 8/1999 | Nagai et al. ............... | 428/690 |
| 5,998,803 A * | 12/1999 | Forrest et al. .............. | 257/40 |
| 6,046,543 A | 4/2000 | Bulovic et al. | |
| 6,099,750 A | 8/2000 | Simmerer et al. | |
| 6,312,838 B1 | 11/2001 | Ishibashi et al. | |
| 6,404,126 B1 | 6/2002 | Arai et al. | |
| 6,436,559 B1 | 8/2002 | Ueno et al. | |
| 6,497,969 B2 | 12/2002 | Kim et al. | |
| 6,501,217 B2 | 12/2002 | Beierlein et al. | |
| 6,602,969 B2 | 8/2003 | Ueda et al. | |
| 6,656,608 B1 | 12/2003 | Kita et al. | |
| 6,720,573 B2 * | 4/2004 | Son et al. .................. | 257/40 |
| 6,875,320 B2 | 4/2005 | Raychaudhuri et al. | |
| 6,953,947 B2 * | 10/2005 | Son et al. .................. | 257/40 |
| 6,963,081 B2 | 11/2005 | Gupta et al. | |
| 6,998,487 B2 | 2/2006 | Kim | |
| 7,538,341 B2 * | 5/2009 | Son et al. .................. | 257/40 |
| 2002/0011782 A1 | 1/2002 | Lee et al. | |
| 2002/0117962 A1 | 8/2002 | Beierlein et al. | |
| 2002/0119297 A1 | 8/2002 | Forrest | |
| 2002/0158242 A1* | 10/2002 | Son et al. .................. | 257/40 |
| 2003/0012890 A1 | 1/2003 | Weber et al. | |
| 2003/0159729 A1 | 8/2003 | Shaheen et al. | |
| 2004/0023060 A1 | 2/2004 | Kim et al. | |
| 2004/0067387 A1 | 4/2004 | Kim | |

| | | | |
|---|---|---|---|
| 2004/0113547 | A1 | 6/2004 | Son et al. |
| 2004/0214038 | A1 | 10/2004 | Kwong et al. |
| 2005/0012465 | A1 | 1/2005 | Uchida |
| 2005/0040390 | A1 | 2/2005 | Pfeiffer et al. |
| 2005/0211977 | A1 | 9/2005 | Hirai et al. |

FOREIGN PATENT DOCUMENTS

| | | |
|---|---|---|
| CN | 1161002 C | 8/2004 |
| EP | 0 390 551 | 10/1990 |
| EP | 0 797 375 A2 | 9/1997 |
| EP | 1 099 744 A2 | 5/2001 |
| EP | 1 179 862 A2 | 2/2002 |
| EP | 1 221 719 | 7/2002 |
| EP | 1 571 709 | 9/2005 |
| GB | 2 400 979 | 10/2004 |
| JP | 06-163158 A | 6/1994 |
| JP | 07-11249 A | 1/1995 |
| JP | 08-167477 A | 6/1996 |
| JP | 2000-223276 | 8/2000 |
| JP | 2002-246184 A | 8/2002 |
| JP | 2005-167175 | 6/2003 |
| KR | 2000-82085 | 12/2000 |
| KR | 1020030067773 | 8/2003 |
| KR | PCT/KR 2005/001381 | 5/2005 |
| TW | 506229 | 4/2004 |
| WO | WO 98/49163 A | 11/1998 |
| WO | WO 99/39393 A1 | 8/1999 |
| WO | WO 01/06576 A1 | 1/2001 |
| WO | WO 01/49806 A1 | 7/2001 |
| WO | WO 03/012890 A2 | 2/2003 |
| WO | WO 2004/054326 | 6/2004 |
| WO | WO 2005/109542 | 11/2005 |
| WO | WO 2006/019270 | 2/2006 |
| WO | WO 2007/011132 | 1/2007 |

OTHER PUBLICATIONS

G. Gu, et al.; "Transparent Organic Light Emitting Devices" 1996 American Institute of Physics.
G. Parthasarathy, et al. "A Metal-Free Cathode for Organic Semiconductor Devices" 1998 American Institute of Physics.
L. S. Hung, et al. "Interface Engineering in Preparation of Organic Surface-Emitting Diodes" 1999 American Institute of Physics.
Chieh-Wei Chen, et al. "An Effective Cathode Structure for Inverted Top-Emitting Organic Light-Emitting Devices" 2004 American Institute of Physics.
Jie Liu, et al. "Efficient Bottom Cathodes for Organic Light-Emitting Devices" 2004 American Institute of Physics.
K. Pierterse et al., "Towards Organic N-Type Semi-Conducting Materials", National American Chemical Society Meeting, Mar. 21-25, 1999.
Kim, J.S. et al., "Indium-tin oxide treatment for single-and double-layer polymeric light-emitting diodes: The relation between the anode physical, chemical, and morphological properties and the device performance", Journ. of Applied Physics, vol. 84, (12), pp. 6859-6870 (Dec. 1998).
Kruger, Jessica et al., "Modification of $TiO_2$ Heterojunctions with Benzoic Acid Derivatives in Hybrid Molecular Solid-State Devices," Advanced Materials, vol. 12 (6), pp. 447-451 (2000).
Chang et al., "Dual-color polymer light-emitting pixels processed by hybrid inkjet printing", Applied Physics Letters, vol. 73 (18), pp. 2561-2563 (Nov. 1998).
Birnstock et al., "Screen-printed passive matrix displays based on light-emitting polymers", Applied Physics Letters, vol. 78, (24), pp. 3905-3907 (Jun. 2001).
J. Cui et al., "Indium Tin Oxide Alternatives—High Work Function Transparent Conducting Oxides As Anodes For Organic Light-Emitting Diodes", pp. 1476-1480, Advanced Materials, 2001, 13, No. 19, (Oct. 2001).

\* cited by examiner

*Primary Examiner*—Khiem D Nguyen
(74) *Attorney, Agent, or Firm*—McKenna Long & Aldridge LLP

(57) ABSTRACT

Disclosed herein are an organic light-emitting device having a structure formed by the sequential deposition of a substrate, a first electrode, at least two organic layers and a second electrode, in which the organic layers include a light-emitting layer, and one of the organic layers, which is in contact with the second electrode, is a buffer layer comprising a compound represented by the following formula 1, as well as a fabrication method thereof:

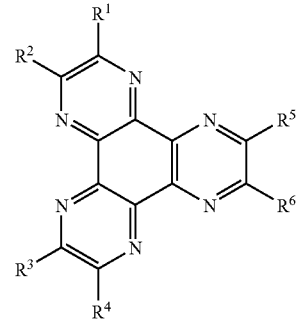

Formula 1 wherein $R^1$ to $R^6$ have the same meanings as defined in the specification. The buffer layer makes it possible to minimize or prevent damage to the organic layer, which can occur when forming the second electrode on the organic layer.

18 Claims, 7 Drawing Sheets

ORGANIC LIGHT-EMITTING DEVICE COMPRISING BUFFER LAYER AND METHOD FOR FABRICATING THE SAME

This application claims the benefit of Korean Patent Application No. 10-2004-0065517, filed Aug. 19, 2004 in Korea, which is incorporated by referenced in its entirety, this application is also a continuation-in-part of U.S application Ser. No. 10/798,584, filed on Mar. 10, 2004, now issued as U.S. Pat. No. 7,535,741, which is a divisional application of U.S. application Ser. No. 09/914,731, filed Aug. 30, 2001, now U.S. Pat. No. 6,720,573, which is a national stage application of International Patent Application PCT/KR00/01537 filed Dec. 27, 2000, that claims priority to Korean Patent Appication No. 2000-82085, filed Dec. 26, 2000, and Korean Patent Application No 1999-067746, filed Dec. 31, 1999.

TECHNICAL FIELD

The present invention relates to an organic light-emitting device and a method for fabricating the same. More particularly, the present invention relates to an organic light-emitting device including a layer for preventing an organic layer from being damaged when forming an electrode on the organic layer in a process of fabricating the organic light-emitting device, and a method for fabricating the same.

BACKGROUND ART

Organic light-emitting devices (OLED) are generally composed of two electrodes (an anode and a cathode) and at least one organic layer located between these electrodes. When voltage is applied between the two electrodes of the organic light-emitting device, holes and electrons are injected into the organic layer from the anode and cathode, respectively, and are recombined in the organic layer to form excitons. In turn, when these excitons decay to their ground state, photons corresponding to the energy difference are emitted. By this principle, the organic light-emitting devices generate visible ray, and they are used in the fabrication of information display devices and illumination devices.

The organic light-emitting devices are classified into three types: a bottom emission type in which light produced in the organic layer is emitted in the direction of a substrate; a top emission type in which the light is emitted in direction opposite the substrate; and a both-side emission type in which the light is emitted in both the direction of the substrate and the direction opposite the substrate.

In passive matrix organic light-emitting device (PMOLED) displays, an anode and a cathode perpendicularly cross each other, and the area of the crossing point acts as a pixel. Thus, the bottom emission and top emission types have no great difference in effective display area ratios (aperture ratios).

However, active matrix organic light-emitting device (AMOLED) displays include thin-film transistors (TFTs) as switching devices for driving the respective pixels. Because the fabrication of these TFTs generally requires a high-temperature process (at least several hundred ° C.), a TFT array required for the driving of organic light-emitting devices is formed on a glass substrate before the deposition of electrodes and organic layers. In this regard, the glass substrate having the TFT array formed thereon is defined as a backplane. When the active matrix organic light-emitting device displays having this backplane are fabricated to have the bottom emission structure, a portion of light emitted toward the substrate is blocked by the TFT array, resulting in a reduction in the effective display aperture ratio. This problem becomes more severe when pluralities of TFTs are given to one pixel in order to fabricate more elaborate displays. For this reason, the active matrix organic light-emitting devices need to be fabricated to have the top emission structure.

In the top emission type or both-side emission type organic light-emitting devices, an electrode located on the opposite side of the substrate without making contact with the substrate must be transparent in the visible ray region. In the organic light-emitting devices, a conductive oxide film made of, for example, indium zinc oxide (IZO) or indium tin oxide (ITO), is used as the transparent electrode. However, this conductive oxide film has a very high work function of generally more than 4.5 eV. For this reason, if the cathode is made of this oxide film, the injection of electrons from the cathode into the organic layer becomes difficult, resulting in a great increase in the operating voltage of the organic light-emitting devices and deteriorations in important device characteristics, such as light emission efficiency. The top emission or both-side emission type organic light-emitting devices need to be fabricated to have the so-called "inverted structure" formed by the sequential lamination of the substrate, the cathode, the organic layer and the anode.

Furthermore, if an a-Si thin-film transistor is used in the active matrix organic light-emitting device, the a-Si TFT has a structure where source and drain junctions are doped with n-type impurities because the a-Si TFT has a physical property such that the main charge carriers are electrons. Thus, in the case of fabricating the active matrix organic light-emitting device with the a-Si TFT, it is preferable in terms of charge injection and process simplification that the active matrix organic light-emitting device is fabricated to have the so-called "inverted structure" by forming the cathode of the organic light-emitting device on the source junction or drain junction of the a-Si TFT formed on the substrate, and then, sequentially forming the organic layer and the anode made of conductive oxide, such as ITO or IZO.

In a process of fabricating the organic light-emitting device with the above-described inverted structure, if the electrode located on the organic layer is formed of a transparent conductive oxide film, such as IZO or ITO, by the use of resistive heating evaporation, the resistive heating evaporation will cause the collapse of the inherent chemical composition ratio of the oxide due to, for example, thermal decomposition during a thermal evaporation procedure. This will result in the loss of characteristics, such as electrical conductivity and visible ray permeability. For this reason, the resistive heating evaporation cannot be used in the deposition of the conductive oxide film, and in most cases, techniques, such as plasma sputtering, are now used.

However, if the electrode is formed on the organic layer by techniques such as sputtering, the organic layer can be damaged due to, for example, electrically charged particles present in plasma used in the sputtering process. Furthermore, the kinetic energy of atoms, which reach the organic layer and form an electrode on the organic layer in the sputtering process, is several tens to several thousands of eV, which is much higher than the kinetic energy of atoms (generally less than 1 eV) in the resistive heating evaporation. Thus, the physical properties of the organic layer can be deteriorated by particle bombardment on the organic layer, resulting in deterioration of electron or hole injection and transport characteristics and light emission characteristics. Particularly, organic materials consisting mainly of covalent bonds of C and H, and thin films made of these materials, are generally very weak against plasma during a sputtering process, compared to inorganic semiconductor materials (e.g., Si, Ge, GaAs, etc.) and, once damaged, the organic materials cannot be returned to their original state.

Thus, in order to fabricate good organic light-emitting devices, damage to the organic layer, which can occur when forming an electrode on the organic layer by a technique, such as sputtering must be minimized or eliminated.

To avoid damage to the organic layer, which can occur when forming an electrode on the organic layer, for example, by sputtering, methods for controlling the rate of thin-film formation are used. For instance, in one method, RF power or DC voltage in an RF or DC sputtering process can be lowered to reduce the number and mean kinetic energy of atoms incident from a sputtering target onto the substrate of the organic light-emitting device, thus reducing sputtering damage to the organic layer.

In another method for preventing sputtering damage to the organic layer, the distance between the sputtering target and the substrate of the organic light-emitting device can be increased to enhance the opportunity of the collisions between atoms, incident to the substrate of the organic light-emitting device from a sputtering target, and sputtering gases (e.g., Ar), thus intentionally reducing the kinetic energy of the atoms.

However, as most of the above-described methods result in a very low deposition rate, the processing time of the sputtering step becomes very long, resulting in a significant reduction in productivity throughout a batch process for fabricating the organic light-emitting device. Furthermore, even in an instance when the sputtering process has a low deposition rate as described above, the possibility of particles having high kinetic energy reaching the surface of the organic layer still exists, and thus, it is difficult to effectively prevent sputtering damage to the organic layer.

"Transparent organic light emitting devices," Applied Physics Letters, May 1996, Volume 68, p. 2606, describes a method of forming an anode and organic layers on a substrate, and then forming a thin layer of mixed metal film of Mg:Ag having excellent electron injection performance thereon, and lastly, forming a cathode using ITO by sputtering deposition thereon. The structure of the organic light-emitting device described in this article is illustrated in FIG. 1. However, the Mg:Ag metal film has shortcomings in that the metal film is lower in visible ray permeability than ITO or IZO and also its process control is somewhat complicated.

"A metal-free cathode for organic semiconductor devices," Applied Physics Letters, Volume 72, April 1998, p. 2138, describes an organic light-emitting device having a structure formed by the sequential lamination of a substrate, a anode, an organic layer and a cathode, where a CuPc layer, relatively resistant to sputtering, is deposited between the organic layer and the cathode in order to prevent sputtering damage to the organic layer, which is caused by the deposition of the cathode. FIG. 2 illustrates the structure of the organic light-emitting device described in the article.

However, while CuPc is generally used to form a hole injection layer, in the above literature, CuPc serves as an electron injection layer in a state damaged by sputtering, between the organic layer and the cathode in the organic light-emitting device with a structure formed by the sequential lamination of the substrate, the anode, the organic layer and the cathode. This deteriorates device characteristics, such as the charge injection characteristic and electric current efficiency of the organic light-emitting device. Furthermore, CuPc has large light absorption in the visible ray region, and thus, increasing the thickness of the CuPc film leads to rapid deterioration of the device performance.

"Interface engineering in preparation of organic surface emitting diodes", Applied Physics Letters, Volume 74, May 1999, p. 3209, describes an attempt to improve the low electron injection characteristic of the CuPc layer by depositing a second electron transport layer (e.g., Li thin film) between an electron transport layer and the CuPc layer. FIG. 3 illustrates the structure of the organic light-emitting device described in this literature. However, this method for preventing sputtering damage has problems in that an additional thin metallic film is required and process control also becomes difficult.

Accordingly, there is a need for the development of technology to prevent the organic layer from being damaged when forming the anode in the organic light-emitting device with the above-described inverted structure.

Meanwhile, an electron injection characteristic from a cathode to an electron transport layer in a regular organic light-emitting device, is improved by depositing a thin LiF layer, which helps the injection of electrons, between the electron transport layer and the cathode. However, the electron injection characteristic is improved only when the method is used in a device in which the cathode is used as a top contact electrode, while the electron injection characteristic is very poor when the method is used in a device having an inverted structure in which the cathode is used as a bottom contact electrode.

"An effective cathode structure for inverted top-emitting organic light-emitting device," Applied Physics Letters, Volume 85, September 2004, p. 2469, describes an attempt to improve the electron injection characteristic through a structure having a very thin Alq3-LiF—Al layer between a cathode and an electron transport layer. However, the structure has a disadvantage that the fabricating process is very complicated. In addition, "Efficient bottom cathodes for organic light-emitting device," Applied Physics Letters, Volume 85, August 2004, p. 837, describes an attempt to improve the electron injection characteristic by depositing a thin Al layer between a metal-halide layer (NaF, CsF, KF) and an electron transport layer. However, the method also has a problem in the process because a new layer must be used.

Accordingly, in an organic light-emitting device having an inverted structure, a method to improve the electron injection characteristic and to simplify the process for fabricating a device is required.

DISCLOSURE

Technical Problem

The present inventors have conducted studies on an organic light-emitting device with a structure formed by the sequential lamination of a substrate, a first electrode, at least two organic layers, and a second electrode, and consequently, found that if one of the organic layers, which is in contact with the second electrode, is formed of an organic material discovered by the present inventors, it is possible to minimize damage to the organic layer, which can occur during the formation of the second electrode. By this, a top emission type or both-side emission type organic light-emitting device having an inverted structure formed by the sequential lamination of a substrate, a cathode, organic layers and an anode can be fabricated without adversely affecting the device characteristics. Moreover, the present inventors have found an electron transport material appropriate to the above organic light-emitting device having an inverted structure and the use of such an electron transport material can simplify the fabricating process of the device and improve the electron injection characteristic.

Therefore, it is an objective of the present invention to provide an organic light-emitting device including a buffer layer capable of preventing an organic layer from being damaged when forming an electrode in the organic light-emitting device and having improved electron injection characteristic, as well as a fabrication method thereof.

Technical Solution

In one embodiment, the present invention provides an organic light-emitting device comprising a substrate, a first electrode, at least two organic layers and a second electrode in the sequentially laminated form, in which the organic layers include a light-emitting layer, and one of the organic layers, which is in contact with the second electrode, is a buffer layer comprising a compound represented by the following formula 1:

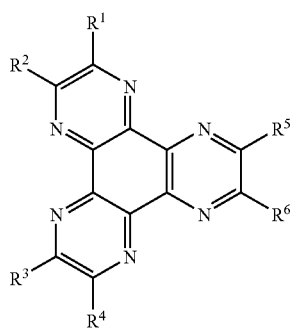

Formula 1 wherein $R^1$ to $R^6$ are each independently selected from the group consisting of hydrogen, halogen atoms, nitrile (—CN), nitro (—$NO_2$), sulfonyl (—$SO_2R$), sulfoxide (—SOR), sulfonamide (—$SO_2NR$), sulfonate (—$SO_3R$), trifluoromethyl (—$CF_3$), ester (—COOR), amide (—CONHR or —CONRR'), substituted or unsubstituted straight or branched chain $C_1$-$C_{12}$ alkoxy, substituted or unsubstituted straight or branched $C_1$-$C_{12}$ alkyl, substituted or unsubstituted aromatic or non-aromatic heterocyclic rings, substituted or unsubstituted aryl, substituted or unsubstituted mono- or di-arylamine, and substituted or unsubstituted aralkylamine, and R and R' are each independently selected from the group consisting of substituted or unsubstituted $C_1$-$C_{60}$ alkyl, substituted or unsubstituted aryl, and substituted or unsubstituted 5-7 membered heterocyclic rings.

In another embodiment of the present invention, the inventive organic light-emitting device is a top emission type or both-side emission type device.

In another embodiment of the present invention, the second electrode in the inventive organic light-emitting device is formed by thin-film formation technology capable of causing damage to the organic layer in the absence of the buffer comprising the compound of formula 1 by involving charges or particles with high kinetic energy.

In another embodiment of the present invention, the second electrode in the inventive organic light-emitting device is formed of a conductive oxide film or metal having work function of 2-6 eV.

In another embodiment, the first electrode in the inventive organic light-emitting device is a cathode, and the second electrode is an anode.

In another embodiment of the present invention, the organic layers in the inventive organic light-emitting device include an electron transport layer and the electron transport layer comprises a material having a group selected from the group consisting of imidazole, oxazole and thiazole.

In yet another embodiment, the present invention provides a method for fabricating an organic light-emitting device, comprising the step of sequentially laminating a first electrode, at least two organic layers and a second electrode on a substrate, in which one of the organic layers is formed as a light-emitting layer, and one of the organic layers, which is in contact with the second electrode, is formed of the compound represented by formula 1.

Advantageous Effects

According to the present invention, damage to the organic layer, which can occur when forming an electrode on the organic layer, can be prevented by the buffer layer comprising the compound of formula 1 below. By this, an organic light-emitting device having a structure formed by the sequential lamination of a substrate, a cathode, organic layers and an anode can be fabricated without damage to the organic layer, which can occur when forming the electrode on the organic layer.

DESCRIPTION OF DRAWINGS

The above and other objects, features and advantages of the present invention will be more clearly understood from the following detailed description taken in conjunction with the accompanying drawings, in which.

MODE FOR INVENTION

Hereinafter, the present invention will be described in detail.

An organic light-emitting device according to the present invention has a structure formed by sequentially laminating a substrate, a first electrode, at least two organic layers and a second electrode, in which the organic layers include a light-emitting layer, and one of the organic layers, which is in contact with the second electrode, is a buffer layer comprising a compound represented by the following formula 1:

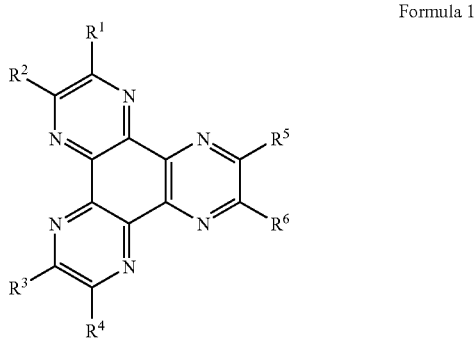

Formula 1 wherein, $R^1$ to $R^6$ are each independently selected from the group consisting of hydrogen, halogen atoms, nitrile (—CN), nitro (—NO$_2$), sulfonyl (—SO$_2$R), sulfoxide (—SOR), sulfonamide (—SO$_2$NR), sulfonate (—SO$_3$R), trifluoromethyl (—CF$_3$), ester (—COOR), amide (—CONHR or —CONRR'), substituted or unsubstituted straight or branched chain C$_1$-C$_{12}$ alkoxy, substituted or unsubstituted straight or branched C$_1$-C$_{12}$ alkyl, substituted or unsubstituted aromatic or non-aromatic heterocyclic rings, substituted or unsubstituted aryl, substituted or unsubstituted mono- or di-arylamine, and substituted or unsubstituted aralkylamine, and R and R' are each independently selected from the group consisting of substituted or unsubstituted C$_1$-C$_{60}$ alkyl, substituted or unsubstituted aryl, and substituted or unsubstituted 5- to 7-membered heterocyclic rings.

Figure 11:
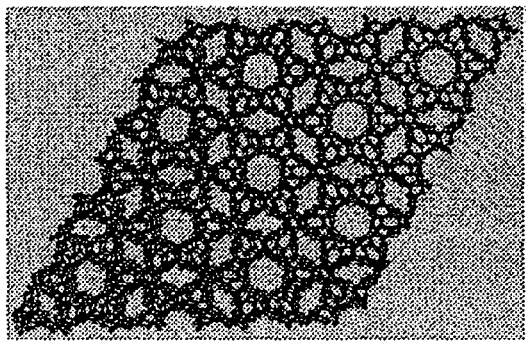
FIG. 11 shows the crystal structure in c-axial of the compound of formula 1-1.
Figure 12:
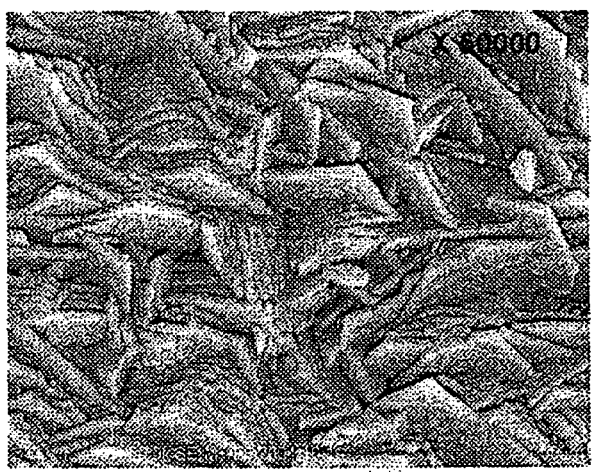
FIG. 12 is SEM image showing the surface of a film consisting of the compound of formula 1-1.

In the inventive organic light-emitting device, the buffer layer comprising the compound of formula 1 is an organic layer in contact with the second electrode, and can prevent the organic layer from being damaged when forming the second electrode on the organic layer during the process of fabricating the organic light-emitting device. For example, if a technique, such as sputtering, is used for the formation of the second electrode, particularly a second transparent electrode, on the organic layer, electrical or physical damage to the organic layer can occur due to electrically charged particles or atoms having high kinetic energy, which are generated in plasma during a sputtering process. This damage to the organic layer can likewise occur when forming an electrode on the organic layer not only by sputtering but also by thin-film formation technology capable of causing damage to the organic layer by involving charges or particles having high kinetic energy. However, when the second electrode is formed on the buffer layer comprising the compound of formula 1 using the above-described method, electrical or physical damage to the organic layer can be minimized or prevented. This can be attributed to the fact that the compound of formula 1 has a higher crystallinity than that of organic materials used in the prior organic light-emitting devices, so that the organic layer comprising the compound has a higher density. FIG. 11 shows the crystal structure in c-axial of the compound of formula 1-1, which is an example of the compound of formula 1. FIG. 12 is SEM image showing the surface of a film formed by the compound of formula 1-1. As shown in FIGS. 11 and 12, the compound of formula 1 is confirmed to have a high crystallinity.

In the present invention, electrical or physical damage to the organic layer can be minimized or prevented as described above, so that the light-emitting characteristics of the device can be prevented from being deteriorated by damage to the organic layer. Also, because it is possible to prevent damage to the organic layer in a process of forming the second electrode, the control of process parameters and the optimization of a process apparatus during the formation of the second electrode becomes easier, so that process productivity throughout can also be improved. Also, the material and deposition method of the second electrode can be selected from a wide range thereof. For example, in addition to a transparent electrode, a thin film made of metal, such as Al, Ag, Mo, Ni, etc. can also be formed by sputtering or by physical vapor deposition (PVD) using laser, ion-beam assisted deposition or similar technologies which can cause damage to the organic layer in the absence of the buffer comprising the compound of formula 1 by involving charges or particles having high kinetic energy.

By the function of the buffer layer comprising the compound of formula 1 in the inventive organic light-emitting device, the material and deposition method of the second electrode can be selected from a wide range thereof. Thus, a top emission type or both-side emission type light-emitting device or an active matrix organic light-emitting device having a-Si TFTs, where a cathode, organic layers and an anode are sequentially laminated on a substrate, can be fabricated without causing damage to the organic layer. Up to now, there has been no disclosure showing the organic light-emitting device having the above-described inverted structure, which has been fabricated without the problem of damage to the organic layer.

In the present invention, the electrical properties of the organic light-emitting device can be improved by the use of a buffer layer comprising the compound of formula 1. For example, the inventive organic light-emitting device shows a reduction in leakage current in a reverse bias state, leading to a remarkable improvement in current-voltage characteristics, and thus, a very clear rectification characteristic. As used herein, the term "rectification characteristic," which is a general characteristic of diodes means that the magnitude of current in a region applied with reverse voltage is much lower than the magnitude of current in a region applied with forward voltage. The compound of formula 1 has excellent crystallinity compared to organic materials, which have been used in the prior organic light-emitting devices as described above so that a layer made of the compound of formula 1 has a high density. Thus, the compound of formula 1 effectively prevents structural defects of molecules or defects to interfacial characteristics, which occur when particles having high kinetic energy are implanted into the inside or interlayer interface of the organic layer by a sputtering process or the like. For this reason, the electrical characteristics, such as rectification characteristic, of the device seem to be maintained.

Figure 10:
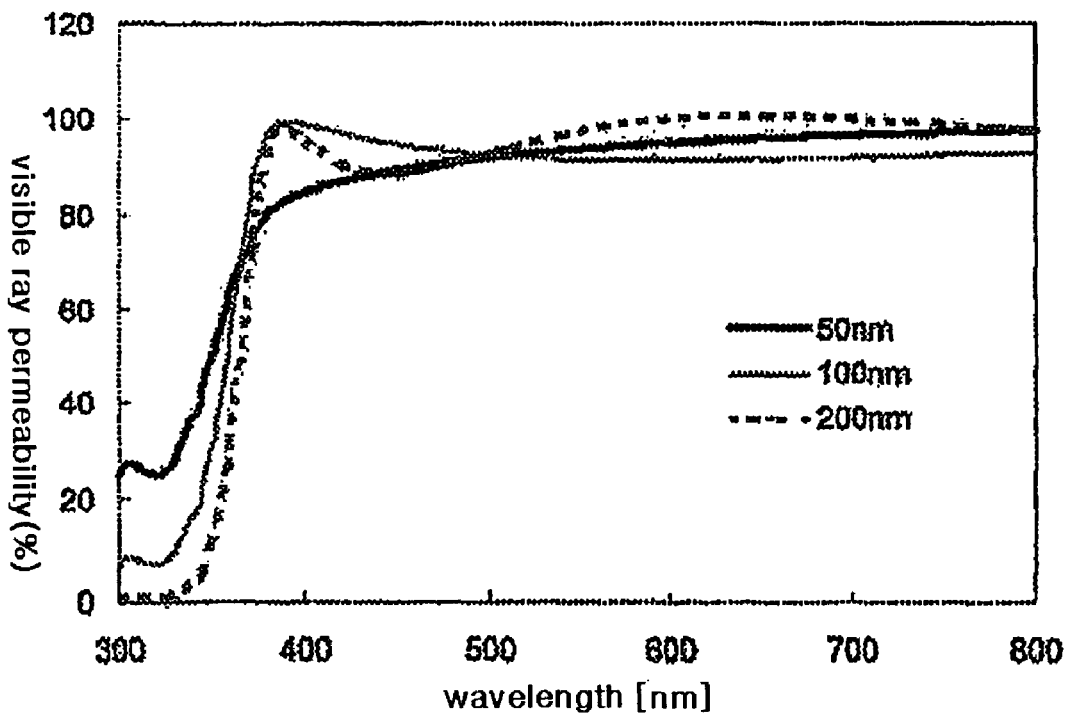
FIG. 10 is a graphic diagram showing visible ray permeability as a function of the deposition thickness of the inventive buffer layer consisting of the compound represented by formula 1.

Also, the buffer layer comprising the compound of formula 1 has higher visible ray permeability than an inorganic layer used in the prior buffer layer that are made of, for example, metal or CuPc, so that its thickness is controlled more variably than the prior buffer layer. FIG. 10 shows permeability in the visible ray region as a function of the thickness of a thin film made of the compound of formula 1. When the inorganic layer which has been used as the buffer layer in the prior art is generally formed to a thickness of 200 nm, it has very low visible ray permeability, however, the layer comprising the compound of formula 1 did not show a reduction in visible ray permeability even when its thickness was 200 nm.

Furthermore, if the second electrode in the inventive organic light-emitting device is an anode, the buffer layer comprising the compound of formula 1 not only functions to prevent sputtering damage but also acts as a hole injection layer for injecting holes from the anode into a hole transport layer or a light-emitting layer or as a charge generation layer for forming hole-electron pairs. Accordingly, the inventive organic light-emitting device can become more efficient without requiring a separate hole injection layer or hole transport layer.

Concrete examples of the compound of formula 1 include compounds represented by the following formulas:

Formula 1-1

Formula 1-2

Formula 1-3

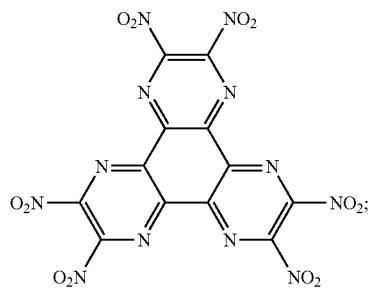

Formula 1-4

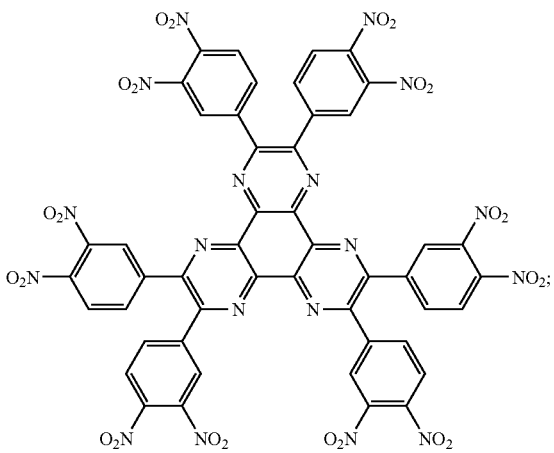

Formula 1-5

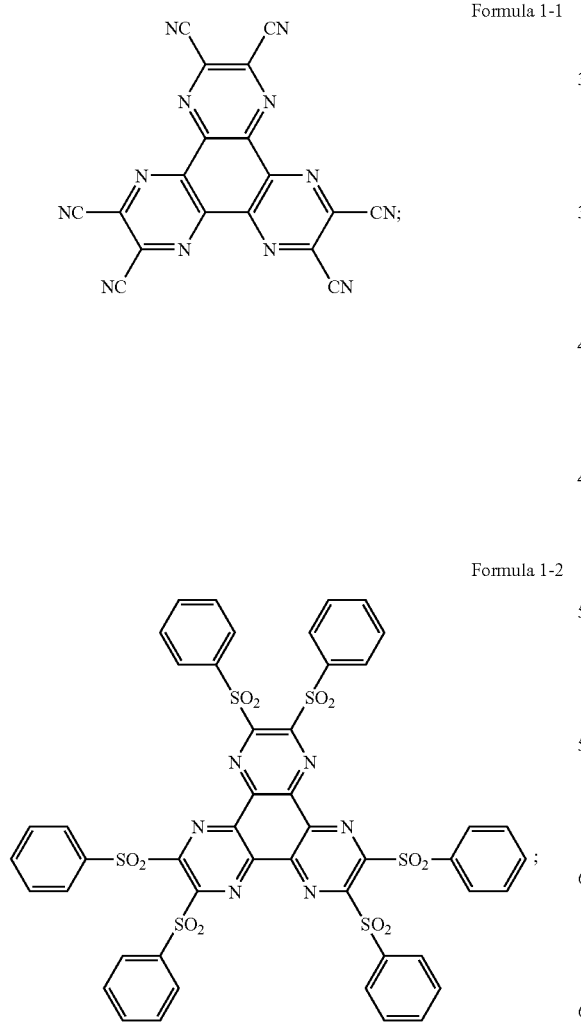

and

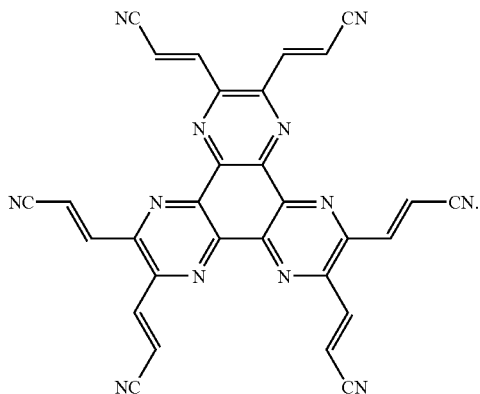

Formula 1-6

Other examples, synthetic methods and various features of the compound of formula 1 are described in the US patent application No. 2002-0158242, U.S. Pat. Nos. 6,436,559 and 4,780,536, the disclosures of which are all incorporated herein by reference.

Figure 6:
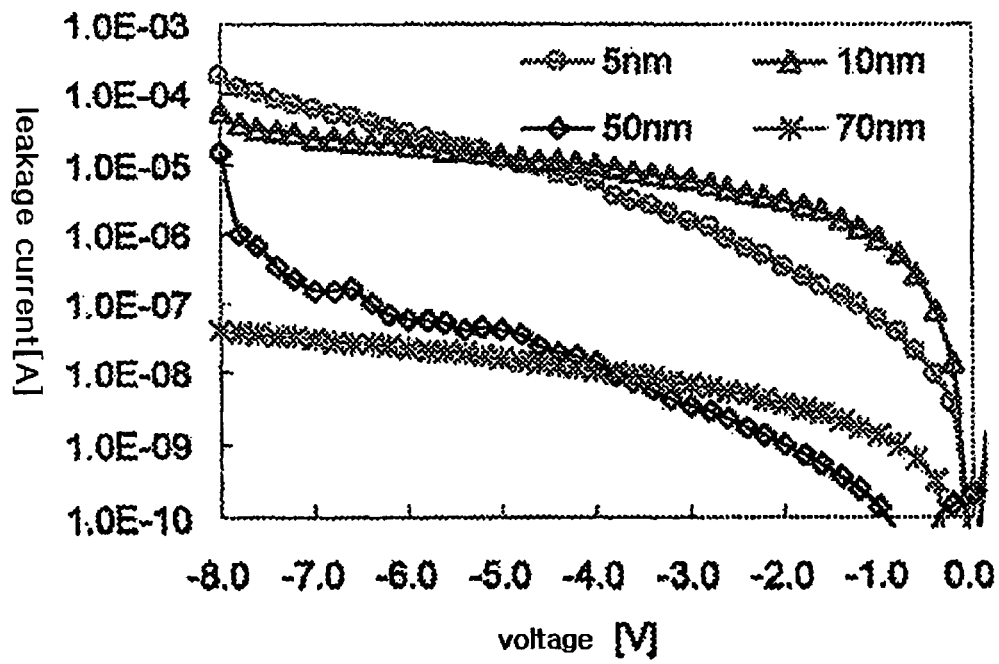
FIG. 6 is a graphic diagram showing a change in the reverse voltage-current (leakage current) characteristic of an organic light-emitting device as a function of the thickness of the inventive buffer layer.

In the present invention, the effect of the buffer layer comprising the compound of formula 1 can be enhanced by increasing its thickness. This is proven by an improvement in the leakage current resulting from an increase in the thickness of the buffer layer. FIG. 6 shows leakage current as a function of the thickness of the buffer layer in contact with the anode in the organic light-emitting device having a structure formed by the sequential lamination of the substrate, the cathode, the organic layers and the anode. As can be seen in FIG. 6, as the thickness of the layer comprising the compound of formula 1 increases from 5-10 nm to 50 nm, the leakage current is rapidly reduced, leading to a remarkable improvement in voltage-current characteristics.

In the present invention, the optimum thickness of the buffer layer comprising the compound of formula 1 may vary depending on sputtering process factors, such as, deposition rate, RF power, DC voltage and the like, used in the formation of the second electrode. For example, in the case of a sputtering process using high voltage and power for rapid deposition, the optimum thickness of the buffer layer increases. In the present invention, the thickness of the buffer layer comprising the compound of formula 1 is preferably equal to or more than 20 nm, and more preferably equal to or more than 50 nm. If the thickness of the buffer layer is less than 20 nm, the layer can function as a hole injection or transport layer, but cannot sufficiently function as the buffer layer. Meanwhile, the thickness of the buffer layer is preferred to be equal to or less than 250 nm. If the thickness of the buffer layer is more than 250 nm, the process time required for the fabrication of the device will become long and the surface shape of the layer comprising the compound of formula 1 will become rough, thus adversely affecting the other characteristics of the device.

In the present invention, the buffer layer comprising the compound of formula 1 can be formed between the anode and the cathode by vacuum deposition or solution application techniques. Examples of the solution application techniques include, but are not limited to, spin coating, dip coating, doctor blading, inkjet printing, thermal transfer techniques, etc. The buffer layer comprising the compound of formula 1 may also additionally comprise other materials, if necessary, and the buffer layer may be formed of a thin film made of a mixture of organic and inorganic materials.

In the present invention, a thin oxide film having an insulating property may be additionally formed between the second electrode and the buffer layer.

Meanwhile, in the inventive organic light-emitting device, the organic layers may include an electron transport layer and the electron transport layer can be formed by the co-deposition of an organic material with a metal having a low work function, such as, Li, Cs, Na, Mg, Sc, Ca, K, Ce, Eu or a thin metal film containing at least one of these metals. However, the electron transport layer in the inventive organic light-emitting device is preferred to comprise a material having a group selected from the group consisting of imidazole, oxazole and thiazole, more preferably imidazole group. Examples of the material include the compound of the following formula 2 having imidazole group, as described in Korean Paten Laid-open Publication 2003-0067773 and the compound of the following formula 3, as described in U.S. Pat. No. 5,645,948, etc. The materials can be co-deposited with a metal having a low work function, such as, Li, Cs, Na, Mg, Sc, Ca, K, Ce, Eu, etc. Korean Paten Laid-open Publication 2003-0067773 and U.S. Pat. No. 5,645,948 entirely are incorporated into this specification.

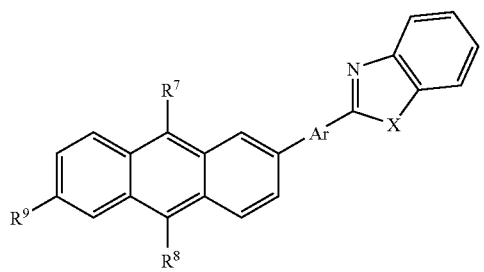

Formula 2 wherein, $R^7$ and $R^8$ are each independently selected from the group consisting of hydrogen, aliphatic hydrocarbons of 1-20 carbon atoms, and aromatic heterocyclic rings or aromatic rings, such as benzene, naphthalene, biphenyl and anthracene, provided that $R^7$ and $R^8$ is not hydrogen concurrently;

Ar is selected from the group consisting of aromatic heterocyclic rings or aromatic rings, such as, benzene, naphthalene, biphenyl and anthracene;

$R^9$ is selected from the group consisting of hydrogen, aliphatic hydrocarbons having 1-6 carbon atoms, and aromatic heterocyclic rings or aromatic rings, such as, substituted benzene, naphthalene, biphenyl and anthracene; and X is selected from the group consisting of O, S and $NR^{10}$ wherein $R^{10}$ is selected from the group consisting of hydrogen, aliphatic hydrocarbons of 1-7 carbon atoms, and aromatic heterocyclic rings or aromatic rings, such as, benzene, naphthalene, biphenyl and anthracene.

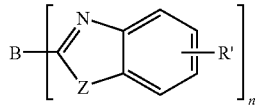

Formula 3 wherein n is an integer of from 3 to 8;

Z is O, S or NR;

R and R' are individually hydrogen; alkyl of 1-24 carbon atoms, for example, propyl, t-butyl, heptyl, and the like; aryl or hetero-atom substituted aryl of 5-20 carbon atoms, for example, phenyl and naphthyl, furyl, thienyl, pyridyl, quinolinyl and other heterocyclic systems; or halo such as chloro, fluoro; or atoms necessary to complete a fused aromatic ring;

B is a linkage unit consisting of alkyl, aryl, substituted alkyl, or substituted aryl, which conjugatedly or unconjugately connects the multiple benzazoles together.

In the present invention, if the electron transport layer is formed to comprise the above material, the inventive device is preferred to include an electron injection layer. The electron injection layer is preferred to a LiF layer.

The inventive organic light-emitting device has a structure formed by the sequential lamination of a substrate, a first electrode, at least two organic layers and a second electrode, and can be fabricated by the use of the same materials and methods as known in the art except that one of the organic layers, which is in contact with the second electrode, is formed as the buffer layer comprising the compound of formula 1.

As described above, in the present invention, there is no specific limitation on methods of forming the second electrode on the buffer layer, and thus, the material and formation process of the second electrode can be selected from a wider range thereof than that of the prior art.

For example, the second electrode in the present invention can be formed by thin-film formation technology capable of causing damage to the organic layer in the absence of the buffer layer comprising the compound of formula 1 by involving charges or particles with high kinetic energy, such as sputtering, physical vapor deposition (PVD) using a laser, ion-beam-assisted deposition or technology similar thereto. Thus, electrode materials, which can be formed into a film only by these techniques may also be used. For example, the second electrode may be formed of a conductive oxide transparent in the visible ray region, such as indium-doped zinc oxide (IZO) or indium-doped tin oxide (ITO), or Al, Ag, Au, Ni, Pd, Ti, Mo, Mg, Ca, Zn, Te, Pt, Ir or an alloy material containing at least one of these metals.

Figure 1:
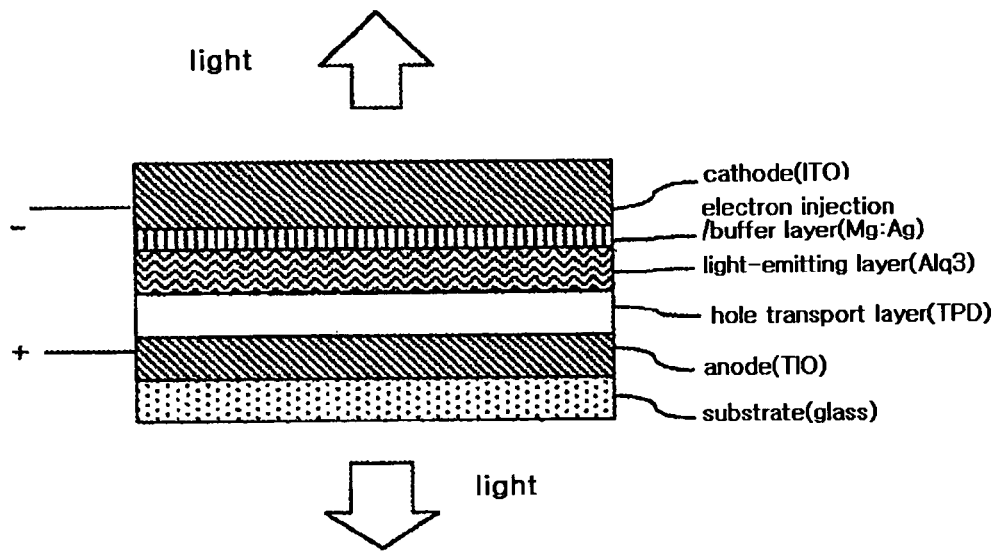
FIG. 1 illustrates the structure of the prior organic light-emitting device formed by sequentially laminating a substrate, an anode, organic layers and a cathode (ITO), in which an Mg:Ag layer is applied between one of the organic layers and the ITO cathode.
Figure 2:
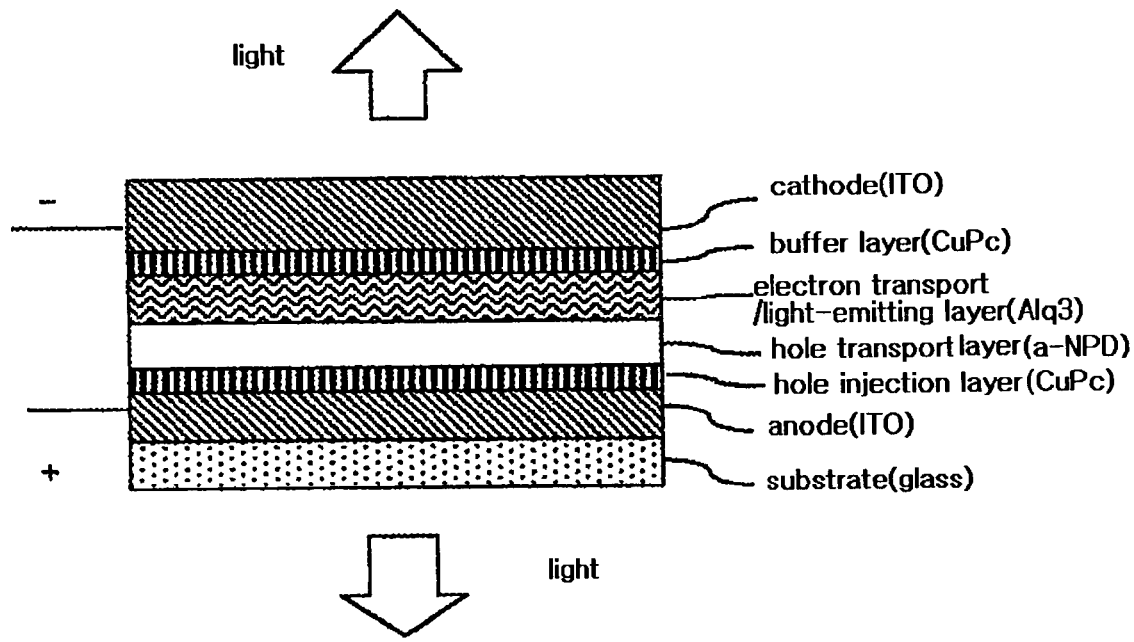
FIG. 2 illustrates the structure of the prior organic light-emitting device formed by sequentially laminating a substrate, an anode, organic layers and a cathode (ITO), in which a CuPc layer is applied between one of the organic layers and the ITO cathode.
Figure 3:
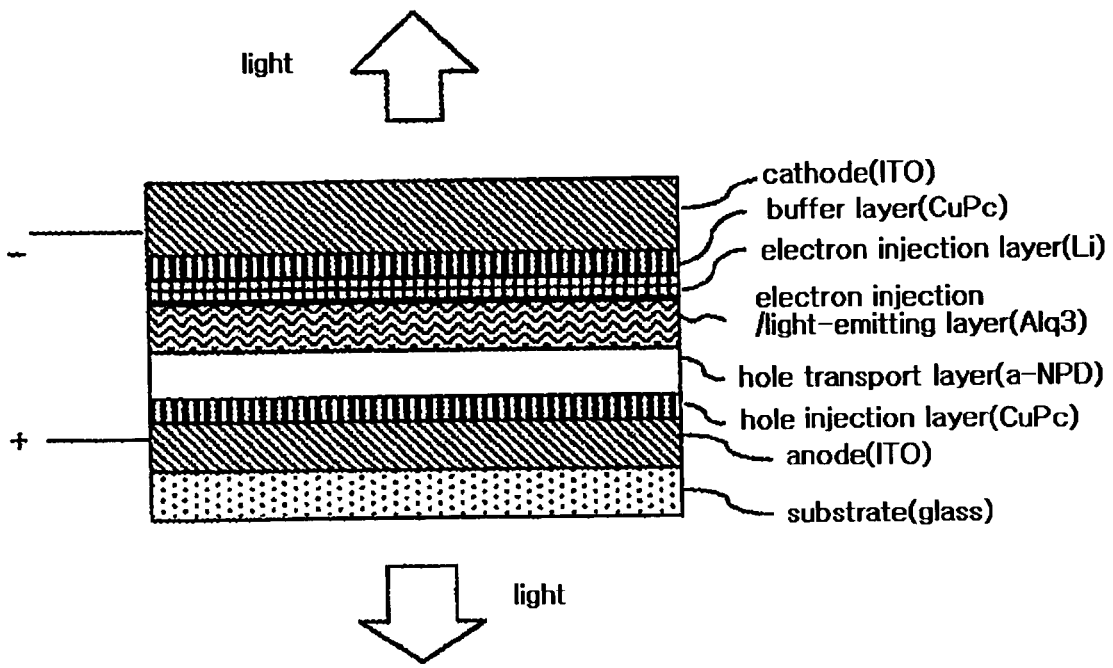
FIG. 3 illustrates the structure of the prior organic light-emitting device shown in FIG. 2, in which a Li thin film (electron injection layer) is laminated as an organic layer in contact with the CuPc layer in the light-emitting device.
Figure 4:
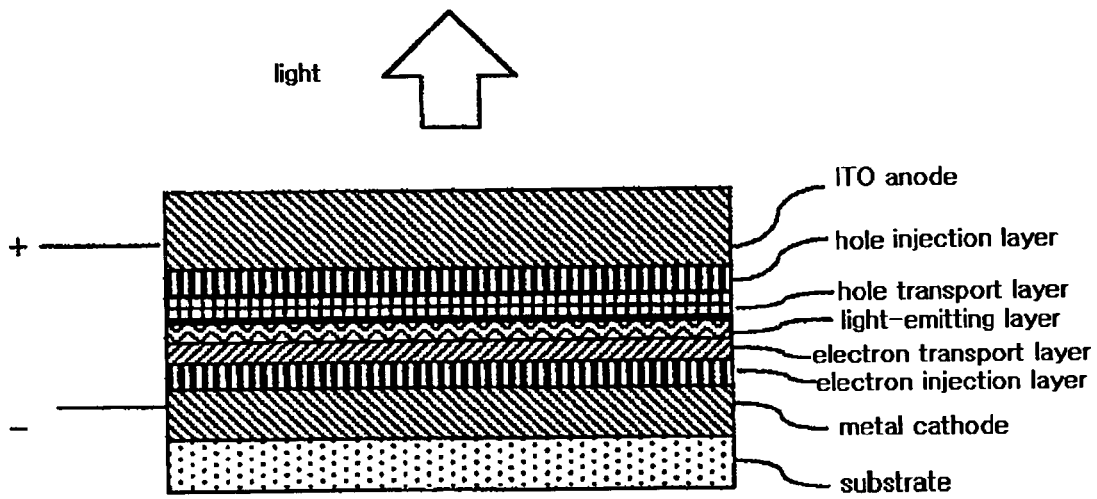
FIG. 4 illustrates the structure of a top emission type organic light-emitting device according to the present invention.
Figure 5:
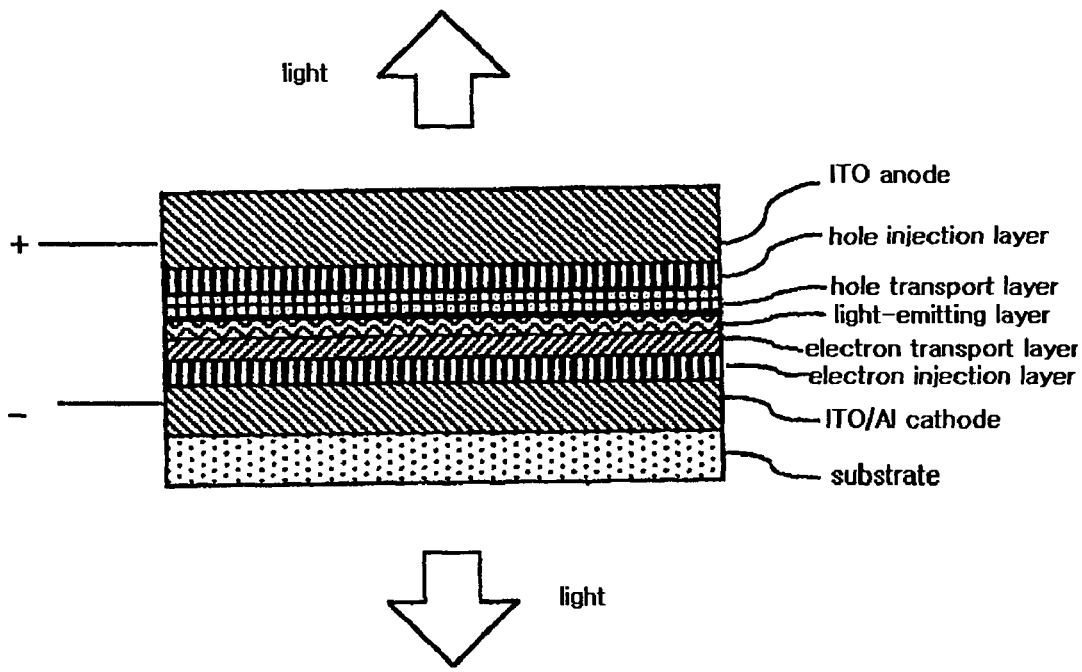
FIG. 5 illustrates the structure of a both-side emission type organic light-emitting device according to the present invention.

Examples of the organic light-emitting device according to the present invention are shown in FIGS. 4 and 5. FIG. 4 illustrates a top emission type light-emitting device, and FIG. 5 illustrates a both-side emission type light-emitting device. However, it will be understood that the structure of the inventive organic light-emitting device is not limited only to these structures.

The organic layers in the inventive organic light-emitting device may consist not only of a monolayer structure but also of a multilayer structure formed by the lamination of at least two organic layers. For example, the inventive organic light-emitting device may have a structure comprising a hole injection layer, a hole transport layer, a light-emitting layer, an electron transport layer, an electron injection layer, a buffer layer formed between an anode and the hole injection layer, and the like as organic layers. However, the structure of the organic light-emitting device is not limited only to this structure and may comprise a smaller number of organic layers.

Hereinafter, the present invention will be described in detail using examples. It is to be understood, however, that these examples are given for illustrative purpose only and are not to be construed to limit the scope of the present invention.

EXAMPLES

Examples 1-5

On a glass substrate, a cathode (Al) having a thickness of 150 nm and an electron injection layer (LiF) having a thickness of 1.5 nm were sequentially formed by a thermal evaporation process. Then, on the electron injection layer, an electron transport layer consisting of a thin film made of a material represented by the following formula 2-1 comprising imidazole group was formed to a thickness of 20 nm.

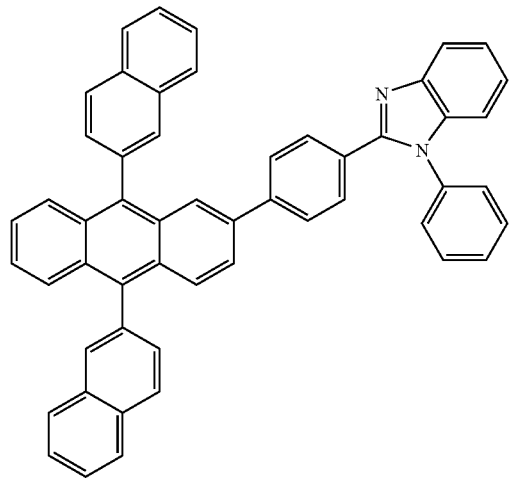

Formula 2-1

Then, on the electron transport layer, an Alq$_3$ light-emitting host was co-deposited with C545T (10-(2-benzothiazolyl)-1, 1,7,7-tetramethyl-2,3,6,7-tetrahyro-1H,5H,11H-1)benzopyrano[6,7,8-ij]quinolizin-11-one) to form a light-emitting layer having a thickness of 30 nm. On the light-emitting layer, a hole transport layer consisting of a thin film made of NPB (4,4'-bis[N-(1-napthyl)-N-phenylamino]biphenyl) was deposited to a thickness of 40 nm. On the hole transport layer, a hole injection/buffer layer made of a compound represented by the following formula 1-1 was formed to a thickness of 5 nm (Example 1), 10 nm (Example 2), 20 nm (Example 3), 50 nm (Example 4) or 70 nm (Example 5):

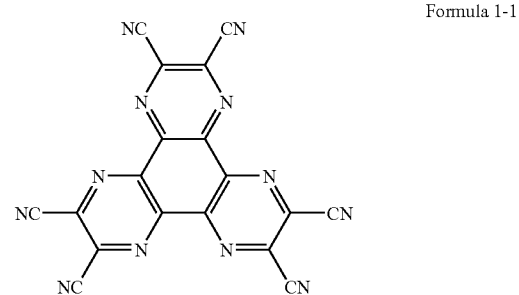

Formula 1-1

On the buffer layer, an IZO anode having a thickness of 150 nm was formed by a sputtering process at a rate of 1.3 Å/sec, thus fabricating a top emission type organic light-emitting device.

Example 6

A both-side emission type organic light-emitting device was fabricated in the same manner as described in Examples 1-5 except that a cathode consisting of an thin Al film having a very small thickness of 5 nm formed on an ITO film having a thickness of 150 nm is used in place of the cathode consisting of the thin Al film having a thickness of 150 nm.

[Measurement of Current-Voltage Characteristics and Light Emission Characteristics of Device]

Figure 7:
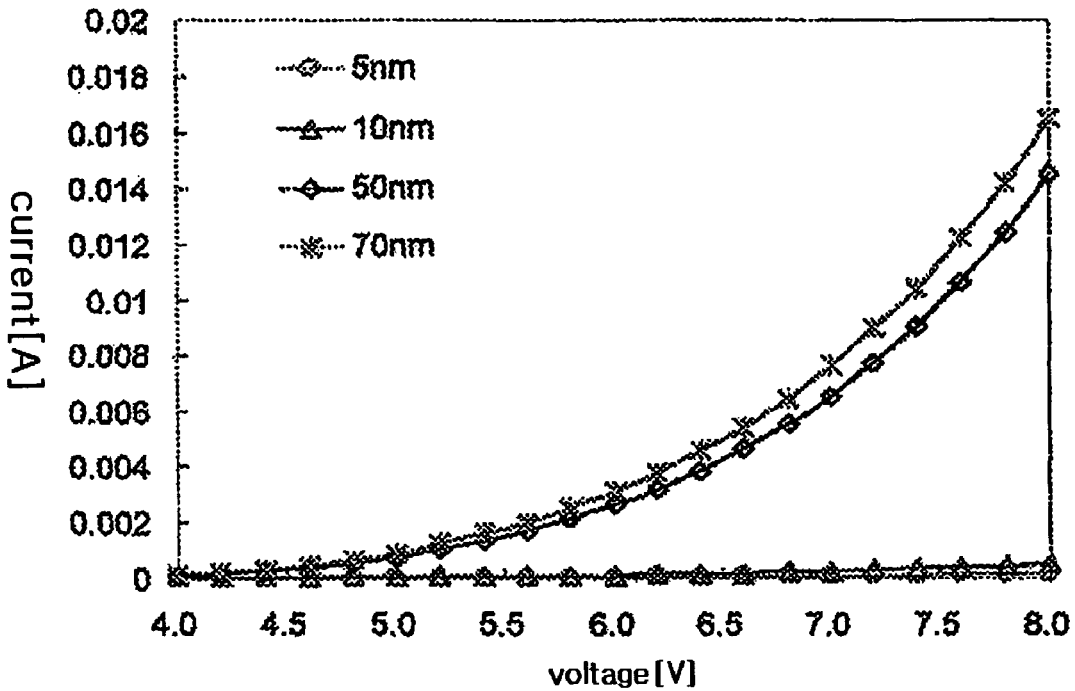
FIG. 7 is a graphic diagram showing a change in the forward voltage-current characteristic of an organic light-emitting device as a function of the thickness of the inventive buffer layer.
Figure 8:
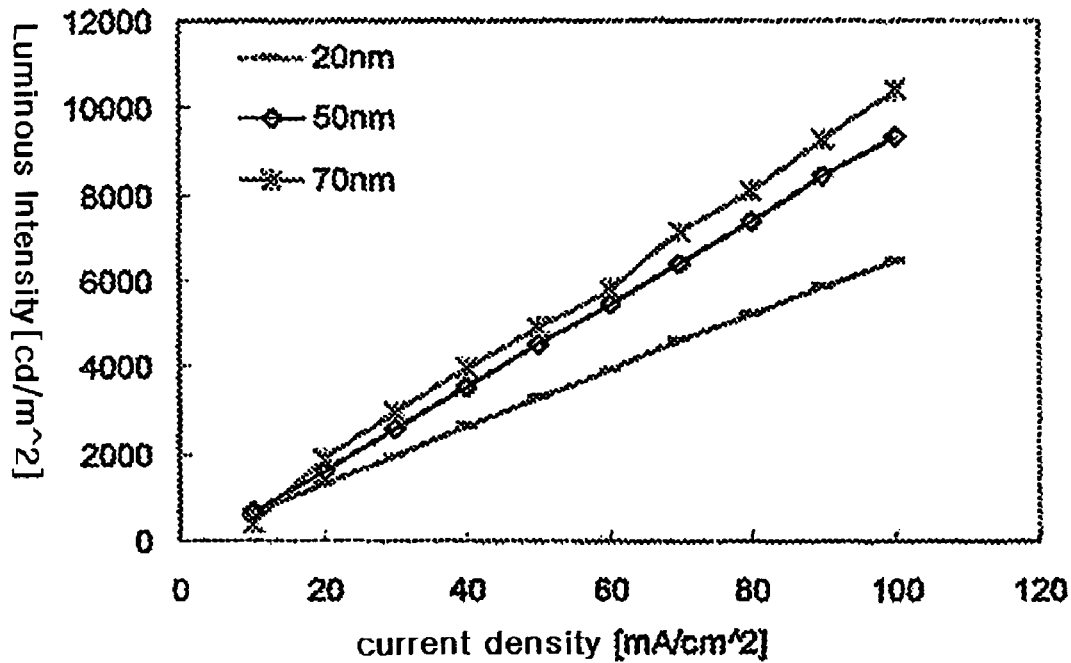
FIG. 8 is a graphic diagram showing the luminous intensity-current density characteristic of an organic light-emitting device as a function of the thickness of the inventive buffer layer.
Figure 9:
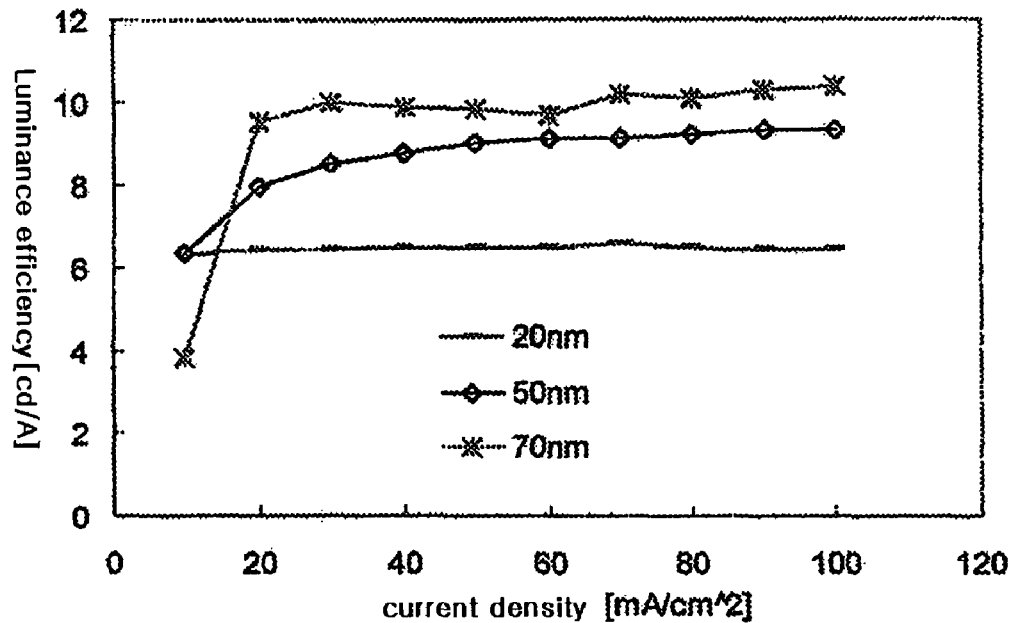
FIG. 9 is a graphic diagram showing the luminance efficiency-current density characteristic of an organic light-emitting device as a function of the thickness of the inventive buffer layer.

To the organic light-emitting device fabricated in Example 1, each of reverse and forward electric fields was applied at a voltage increasing at increments of 0.2 volts while current at each voltage value was measured. The measurement results are shown in FIGS. 6 and 7, respectively. Also, to the organic light-emitting device fabricated in Example 1, current was applied while gradually increasing current density from 10 mA/cm$^2$ to 100 mA/cm$^2$, and at the same time, the luminous intensity of the device was measured using photometry. The measurement results are shown in FIGS. 8 and 9.

In organic light-emitting devices, damage to an organic layer occurring in the formation of an electrode leads to deterioration in current-voltage characteristics and light emission characteristics. Thus, the current-voltage characteristics and light emission characteristics shown in FIGS. 6 to 9 indicate that the compound of formula 1 has the effect of preventing damage to the organic layer.

FIGS. 6 and 7 show the current-voltage characteristics of the organic light-emitting device as a function of the thickness of the inventive buffer layer. It is known that when an organic layer in contact with the second electrode located opposite the substrate is made of an organic material, which has been generally used in the prior organic light-emitting device, an organic light-emitting device comprising this organic layer will not show normal rectification and light emission characteristics due to the damage to the organic layer, which occurs when forming the second layer on the organic layer by sputtering. However, as shown in FIGS. 6 and 7, the inherent characteristics (e.g., rectification characteristic) of the organic light-emitting device were clearly shown as the thickness of the buffer layer made of the compound of formula 1 increased.

Regarding a reverse current-voltage characteristic shown in FIG. 6, the case of forming the buffer layer to a thickness of about 5-10 nm showed little improvement in the leakage current of the device, and the case of forming the buffer layer to a thickness of more than 50 nm showed a remarkable improvement in the leakage current of the device, indicating a very clear rectification characteristic. Regarding a forward current-voltage characteristic shown in FIG. 7, when the thickness of the layer made of the compound of formula 1 was increased from 10 nm to 50 nm, current was consequently increased rapidly.

Furthermore, as shown in FIG. 8, a light emission characteristic was also improved in proportion to an increase in the current as described above. Regarding luminance efficiency shown in FIG. 9, an increase in the thickness of the buffer layer comprising the compound of formula 1 showed a remarkable increase in luminance efficiency. This is attributable to the effect of the buffer layer of preventing sputtering damage.

Example 7

On a glass substrate, a cathode (Al) having a thickness of 150 nm and an electron injection layer (LiF) having a thickness of 1.5 nm were sequentially formed by a thermal evaporation process. Then, on the electron injection layer, an electron transport layer consisting of a thin film made of the material comprising imidazole group represented by the above formula 2-1 was formed to a thickness of 150 nm. On the electron transport layer, an electron injection layer (LiF) having a thickness of 1.5 nm and Al layer having a thickness of 150 nm were formed sequentially to fabricate a symmetrical-type device as shown in FIG. 13 in which electric current runs only through electrons.

Comparative Example 1

Figure 13:
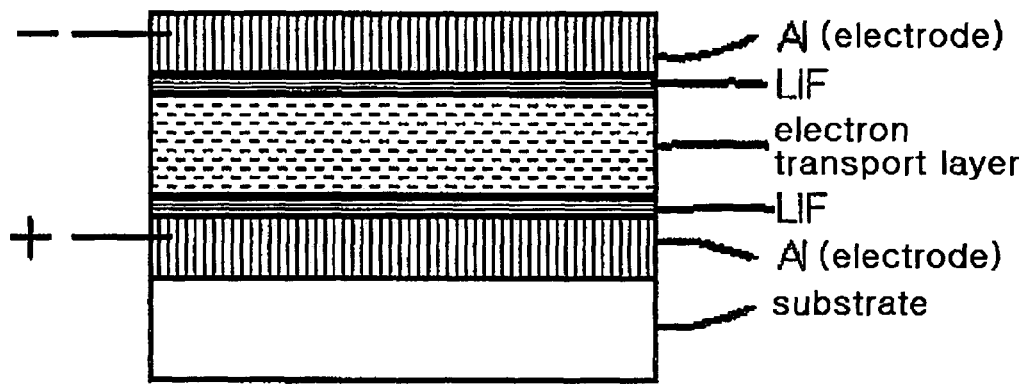
FIG. 13 illustrates a structure of a device having a symmetrical structure consisting of Al—LiF-electron transport layer-LiF—Al fabricated in Example 7.

A symmetrical-type device, as shown in FIG. 13 in which electric current runs only through electrons, was fabricated in the same manner as described in Example 7, except that Alq3 in place of the compound of formula 2-1 was used in forming an electron transport layer.

[Measurement of Current-Voltage Characteristic of the Device]

Example 7 and Comparative Example 1 were symmetrical-type devices having the structure of Al—LiF-electron transport material-LiF—Al, in which the electric current running through the electron transport material is generated only by electrons.

Figure 14:
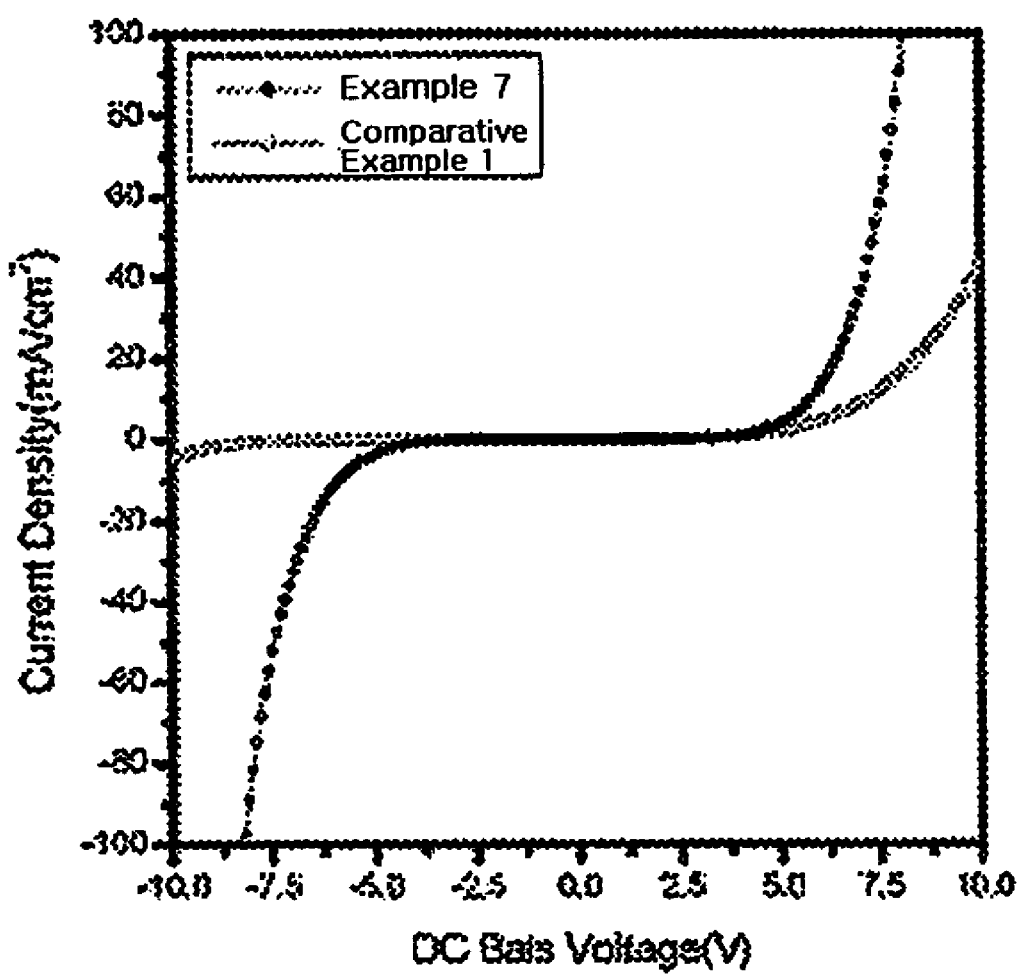
FIG. 14 is a graphic diagram showing a forward voltage-current characteristic and reverse voltage-current characteristic by electrons in the device having a symmetrical structure fabricated in Example 7.

FIG. 14 shows current-voltage characteristic in Example 7 and Comparative Example 1. In FIG. 14, the positive voltage shows electron injection from top Al electrode to the electron transport layer and the negative voltage shows electron injection from bottom Al electrode to the electron transport layer. In Comparative Example 1 that used Alq3 which is frequently used in organic light-emitting device as an electron transport material, electron injection from top Al electrode took place very well while electron injection from bottom Al electrode did not take place very well in spite of a symmetrical-type device. On the other hand, in Example 7 that used the compound of formula 2-1 as an electron transport material, current voltage characteristic is symmetrical and this means that electron injection from both of top Al electrode and bottom Al electrode to the electron transport layer took place very well.

The reason that the electron injection from the bottom electrode to the electron transport layer took place more effectively through the compound of formula 2-1 than Alq3 is considered as the reactivity of imidazole group in the compound of formula 2-1 to Li ion in Li-fluoride (LiF) is larger than that of Alq3. Accordingly, when a material having a group of a large reactivity to Li ion, such as, the imidazole group, is used as an electron transport material, electron injection characteristic from bottom electrode to electron transport layer can be improved.

An organic light-emitting device having an inverted structure requires electron injection from bottom electrode to electron transport layer. Accordingly, if an electron transport material comprising imidazole, or, oxazole or thiazole having similar properties to imidazole, such as the compound of formula 2 or 3, as described above, is used, an organic light-emitting device having improved electron injection characteristic can be provided.

INDUSTRIAL APPLICABILITY

According to the present invention, damage to the organic layer, which can occur when forming an electrode on the organic layer, can be prevented by the buffer layer comprising the compound of formula 1. By this, an organic light-emitting device having a structure formed by the sequential lamination of a substrate, a cathode, organic layers and an anode can be fabricated without damage to the organic layer, which can occur when forming the electrode on the organic layer. In addition, in the organic light-emitting device having an inverted structure, if an electron transport material comprising imidazole, oxazole or thiazole, such as, the compound of formula 2 or 3, is used, electron injection characteristic from the bottom cathode to the electron transport layer is improved and an organic light-emitting device of an inverted structure operating at a low voltage can be provided.

Although a preferred embodiment of the present invention has been described for illustrative purposes, those skilled in the art will appreciate that various modifications, additions and substitutions are possible without departing from the scope and spirit of the invention as disclosed in the accompanying claims.

The invention claimed is:

1. An organic light-emitting device comprising a substrate, a first electrode, at least two organic layers and a second electrode in the sequentially laminated form, in which the organic layers include a light-emitting layer, and one of the organic layers, which is in contact with the second electrode, is a buffer layer comprising a compound represented by the following formula 1:

Formula 1

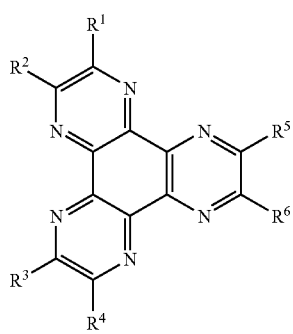

wherein $R^1$ to $R^6$ are each independently selected from the group consisting of hydrogen, halogen atoms, nitrile (—CN), nitro (—NO$_2$), sulfonyl (—SO$_2$R), sulfoxide (—SOR), sulfonamide (—SO$_2$NR), sulfonate (—SO$_3$R), trifluoromethyl (—CF$_3$), ester (—COOR), amide (—CONHR or —CONRR'), substituted or unsubstituted straight or branched chain $C_1$-$C_{12}$ alkoxy, substituted or unsubstituted straight or branched $C_1$-$C_{12}$ alkyl, substituted or unsubstituted aromatic or non-aromatic heterocyclic rings, substituted or unsubstituted aryl, substituted or unsubstituted mono- or di-arylamine, and substituted or unsubstituted aralkylamine, and R and R' are each independently selected from the group consisting of substituted or unsubstituted $C_1$-$C_{60}$ alkyl, substituted or unsubstituted aryl, and substituted or unsubstituted 5-7 membered heterocyclic rings.

2. The organic light-emitting device of claim 1, wherein the compound of formula 1 is selected from compounds represented by the following formulas 1-1 to 1-6:

Formula 1-1

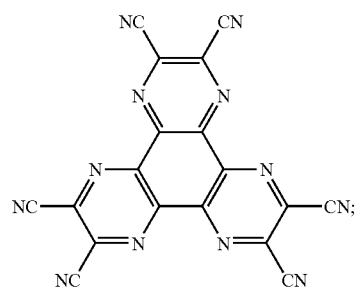

Formula 1-2

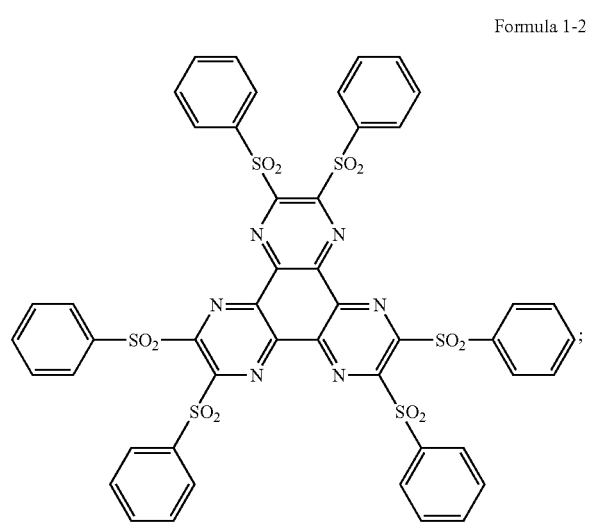

Formula 1-3

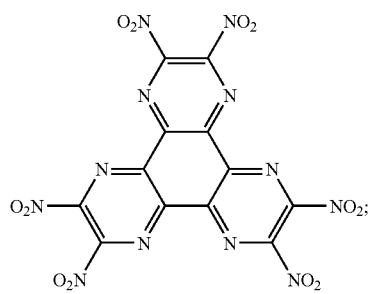

Formula 1-4

Formula 1-5

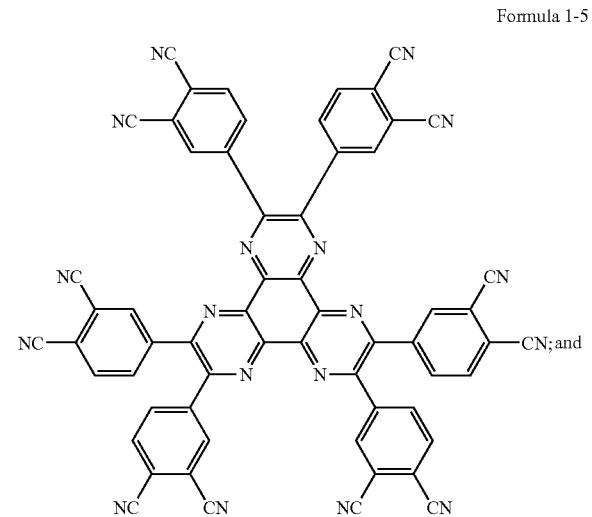

Formula 1-6

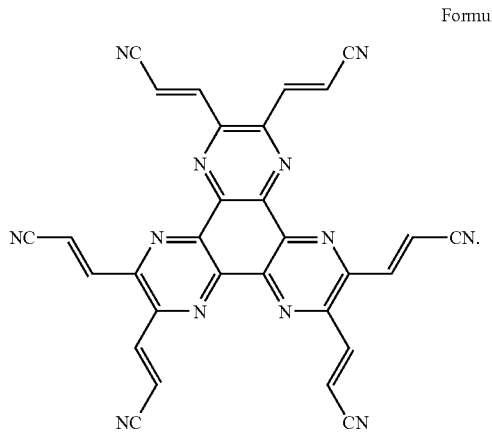

3. The organic light-emitting device of claim 1, wherein the organic light-emitting device is a top emission type or both-side emission type light-emission device.

4. The organic light-emitting device of claim 1, wherein the second electrode is formed by thin-film formation technology capable of causing damage to the organic layer in the absence of the buffer layer comprising the compound of formula 1 by involving charges or particles with high kinetic energy.

5. The organic light-emitting device of claim 4, wherein the thin-film formation technology is selected from the group consisting of sputtering, physical vapor deposition (PVD) using a laser, and ion-beam assisted deposition.

6. The organic light-emitting device of claim 1, wherein the first electrode is a cathode, the second electrode is an anode, and the device is fabricated by forming the cathode on the substrate and then sequentially forming the organic layers and the anode on the cathode.

7. The organic light-emitting device of claim 1, wherein the second electrode is made of a conductive oxide film or metal having work function of 2-6 eV.

8. The organic light-emitting device of claim 7, wherein the second electrode is made of ITO (indium tin oxide).

9. The organic light-emitting device of claim 7, wherein the second electrode is made of IZO (indium zinc oxide).

10. The organic light-emitting device of claim 1, wherein an thin oxide film having an insulating property is additionally formed between the second electrode and the buffer layer.

11. The organic light-emitting device of claim 1, wherein the buffer layer also serves as a hole injection layer.

12. The organic light-emitting device of claim 1, wherein the buffer layer comprising the compound of formula 1 has a thickness of equal to or more than 20 nm.

13. The organic light-emitting device of claim 1, wherein the organic layers include an electron transport layer and the electron transport layer comprising a material having a group selected from the group consisting of imidazole, oxazole and thiazole.

14. The organic light-emitting device of claim 13, wherein the electron transport layer comprising a compound selected from the group consisting a compound of the formula 2 below and a compound of the formula 3 below:

Formula 2

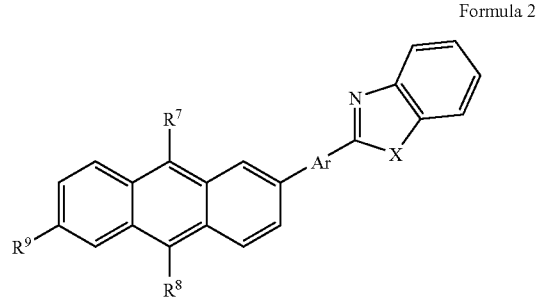

wherein, $R^7$ and $R^8$ are each independently selected from the group consisting of hydrogen, aliphatic hydrocarbons of 1-20 carbon atoms, and aromatic heterocyclic rings or aromatic rings, provided that $R^7$ and $R^8$ is not hydrogen concurrently;

Ar is selected from the group consisting of aromatic heterocyclic rings or aromatic rings;

$R^9$ is selected from the group consisting of hydrogen, aliphatic hydrocarbons having 1-6 carbon atoms, and aromatic heterocyclic rings or aromatic rings; and X is selected from the group consisting of O, S and $NR^{10}$ wherein $R^{10}$ is selected from the group consisting of hydrogen, aliphatic hydrocarbons of 1-7 carbon atoms, and aromatic heterocyclic rings or aromatic rings.

Formula 3

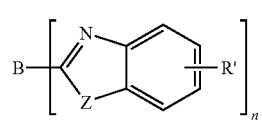

wherein n is an integer of from 3 to 8;

Z is O, S or NR;

R and R' are individually hydrogen; alkyl of 1-24 carbon atoms; aryl or hetero-atom substituted aryl of 5-20 carbon atoms; or halo; or atoms necessary to complete a fused aromatic ring;

B is a linkage unit consisting of alkyl, aryl, substituted alkyl, or substituted aryl, which conjugatedly or unconjugately connects the multiple benzazoles together.

15. The organic light-emitting device of claim 13, wherein an electron injection layer is formed between the first electrode and the electron transport layer.

16. The organic light-emitting device of claim 15, wherein the electron injection layer is a LiF layer.

17. A method for fabricating an organic light-emitting device, comprising the step of sequentially laminating a first electrode, at least two organic layers and a second electrode on a substrate, in which one of the organic layers is formed as a light-emitting layer, and one of the organic layers, which is in contact with the second electrode, is formed from a compound represented by the following formula 1:

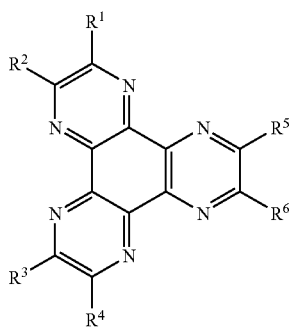

Formula 1 wherein R¹ to R⁶ are each independently selected from the group consisting of hydrogen, halogen atoms, nitrile (—CN), nitro (—NO₂), sulfonyl (—SO₂R), sulfoxide (—SOR), sulfonamide (—SO₂NR), sulfonate (—SO₃R), trifluoromethyl (—CF₃), ester (—COOR), amide (—CONHR or —CONRR'), substituted or unsubstituted straight or branched chain $C_1$-$C_{12}$ alkoxy, substituted or unsubstituted straight or branched $C_1$-$C_{12}$ alkyl, substituted or unsubstituted aromatic or non-aromatic heterocyclic rings, substituted or unsubstituted aryl, substituted or unsubstituted mono- or di-arylamine, and substituted or unsubstituted aralkylamine, and R and R' are each independently selected from the group consisting of substituted or unsubstituted $C_1$-$C_{60}$ alkyl, substituted or unsubstituted aryl, and substituted or unsubstituted 5-7 membered heterocyclic rings.

18. The method of claim 17, wherein the second electrode is formed by thin-film formation technology capable of causing damage to the organic layer in the absence of the layer comprising the compound of formula 1 by involving charges or particles having high kinetic energy.

* * * * *